United States Patent [19]
Colligan

[11] Patent Number: 5,462,543
[45] Date of Patent: * Oct. 31, 1995

[54] APPARATUS FOR ATTACHING SURGICAL SUTURE COMPONENTS

[75] Inventor: Francis D. Colligan, Waterbury, Conn.

[73] Assignee: United States Surgical Corporation, Norwalk, Conn.

[*] Notice: The portion of the term of this patent subsequent to Sep. 27, 2011, has been disclaimed.

[21] Appl. No.: 257,397

[22] Filed: Jun. 9, 1994

Related U.S. Application Data

[63] Continuation of Ser. No. 959,114, Oct. 9, 1992, Pat. No. 5,350,373.

[51] Int. Cl.$^6$ .................................................. A61B 17/00
[52] U.S. Cl. ................. 606/1; 606/224; 72/399; 72/402
[58] Field of Search ................. 606/1, 222, 224, 606/225, 226; 223/102, 104; 163/5; 72/401, 402, 406, 399, 452; 29/516, 517, 243, 748, 753

[56] References Cited

U.S. PATENT DOCUMENTS

| | | |
|---|---|---|
| Re. 27,735 | 8/1973 | Shave et al. . |
| Re. 31,084 | 11/1982 | Birks . |
| 1,558,037 | 10/1925 | Morton . |
| 1,578,543 | 3/1926 | Montgomery . |
| 2,000,680 | 5/1935 | Weatherhead, Jr. . |
| 2,067,568 | 1/1937 | Grünthal . |
| 2,205,893 | 6/1940 | Unger . |
| 2,411,079 | 11/1946 | Baule . |
| 2,620,028 | 12/1952 | Kohut . |
| 2,813,442 | 11/1957 | Wingate . |
| 2,958,929 | 11/1960 | Vineberg et al. . |
| 2,983,898 | 5/1961 | Kalmar et al. . |
| 3,055,412 | 9/1962 | Dibner . |
| 3,130,489 | 4/1964 | Schlage . |
| 3,251,216 | 5/1966 | Broske . |
| 3,253,328 | 5/1966 | Baldwin . |
| 3,365,927 | 1/1968 | Lynch . |
| 3,643,327 | 2/1972 | Jackson . |
| 3,771,343 | 11/1973 | Dawson . |
| 3,871,206 | 3/1975 | Otoda et al. . |
| 3,890,975 | 6/1975 | McGregor . |
| 3,910,282 | 10/1975 | Messer et al. . |
| 3,963,031 | 6/1976 | Hunter . |
| 3,972,219 | 8/1976 | Riehl . |
| 3,980,177 | 9/1976 | McGregor . |
| 4,054,144 | 10/1977 | Hoffman et al. . |
| 4,060,885 | 12/1977 | Hoffman et al. . |
| 4,067,224 | 1/1978 | Birks . |
| 4,072,041 | 2/1978 | Hoffman et al. . |
| 4,192,171 | 3/1980 | Hamilton . |
| 4,229,963 | 10/1980 | Savinov . |
| 4,292,833 | 10/1981 | Lapp . |
| 4,306,443 | 12/1981 | Matsutani . |
| 4,361,948 | 12/1982 | Omata . |
| 4,498,222 | 2/1985 | Ono et al. . |
| 4,567,650 | 2/1986 | Balyasny et al. . |
| 4,719,789 | 1/1988 | Wiebe et al. . |
| 4,722,384 | 2/1988 | Matsutani . |
| 4,799,311 | 1/1989 | Matsutani . |

(List continued on next page.)

FOREIGN PATENT DOCUMENTS

| | | |
|---|---|---|
| 0249504 | 12/1987 | European Pat. Off. . |
| 0296776 | 12/1988 | European Pat. Off. . |
| 8715099 | 3/1988 | Germany . |
| 3805772 | 9/1988 | Germany . |
| 0212027 | 9/1988 | Japan . |
| 63-299834 | 12/1988 | Japan . |
| 1526222 | 9/1978 | United Kingdom . |
| 8203579 | 10/1982 | WIPO . |

*Primary Examiner*—Stephen C. Pellegrino
*Assistant Examiner*—Jeffrey A. Schmidt

[57] ABSTRACT

The present invention relates to an apparatus for attaching surgical sutures to eyeless surgical needles. The apparatus includes a frame for positioning and maintaining the needle while the suture is being attached and a rotating die system which selectively impacts the needle to secure the suture thereto.

21 Claims, 17 Drawing Sheets

U.S. PATENT DOCUMENTS

| | | |
|---|---|---|
| 4,836,006 | 6/1989 | Brown . |
| 4,922,904 | 5/1990 | Uetake et al. . |
| 5,038,461 | 8/1991 | Cerda . |
| 5,046,350 | 9/1991 | Proto et al. . |
| 5,099,676 | 3/1992 | Proto et al. . |
| 5,115,904 | 5/1992 | Folk et al. . |
| 5,131,131 | 7/1992 | Proto et al. . |
| 5,168,619 | 12/1992 | Proto et al. . |
| 5,230,352 | 7/1993 | Putnam et al. . |

APPARATUS FOR ATTACHING SURGICAL SUTURE COMPONENTS

This is a continuation of U.S. application Ser. No. 07/959,144, filed Oct. 9, 1992, now U.S. Pat. No. 5,350,373.

BACKGROUND OF THE INVENTION

1. Field of the Invention

The present invention relates to surgical sutures and their production. More particularly, the invention relates to an apparatus and method for attaching surgical needles to surgical sutures.

2. Description of the Related Art

The trend to develop and produce surgical sutures attached to eyeless surgical needles is continuously evolving. The most common surgical suture of this type is a single-use needle of appropriate size and shape which is attached to the end of the suture, so that the needle is used once and then discarded.

The attachment can be accomplished by use of a "drilled end" needle, that is, one in which a concentric aperture is formed in the end face of the needle, in which the suture is placed in the aperture and the needle is crimped around the suture. Alternatively, a "flanged" needle may be utilized in which a U-shaped channel is stamped into the end of the needle with the ends of the "U" being crimped about the suture to hold the suture together. The attachment must be one which is predictably secure, causes a minimum of damage to tissue, is convenient for the using surgeon, permits sterilization and entails reasonable costs. In addition, the attachment must withstand the rigors of manufacture, sterilization, storage, shipment and use.

With conventional crimping operations a crimp is created between several dies which close to a fixed gap. Any variation in the crimping dies, the needle size, the hole size, or the suture size alters the degree of crimp.

Conventional crimping methods require the back end of the needle be struck with two half moon shaped dies. The needle is then manually rotated 90° and the needle is struck again with the dies. The manual intervention in the production of surgical sutures with eyeless needles reduces production efficiency and increases the associated costs incurred in their manufacture.

To date, techniques devised for connecting such suture components in a manner to perform within the preferred guidelines are not as effective for high speed production of surgical sutures as would otherwise be desirable. The present invention avoids the aforementioned disadvantages and provides a needle crimping apparatus which automatically rotates the dies 90° so as to reduce the need for manual rotation of the needle as described above.

SUMMARY OF THE INVENTION

The present invention relates to an apparatus for attaching surgical sutures to eyeless surgical needles which includes support means, die means attached to the support means for selectively impacting the needle so that a portion of the needle is deformed to maintain the suture therein, the die means being rotatable between at least two positions. First drive means is provided for actuating the die means to impact the needle, and second drive means is provided for rotating the die means at least to a second position respective to the needle are also provided.

Generally, the die means includes a die cartridge having at least one jaw slidably secured thereto and gear means secured to the die cartridge and operatively connected to the second drive means for translating movement of the second drive means to rotational movement of the die cartridge.

The first drive means includes a first pair of arms pivotally connected to a first drive member and positioned adjacent the die cartridge on opposite sides thereof and a second pair of arms pivotally connected to the first drive member and positioned adjacent the die cartridge on opposite sides thereof and out of phase with the first pair of arms.

The second drive means is adapted to rotate the die means between the first and second positions. In the preferred embodiment, the die means is adapted to impact the needle in the first and second positions, where the second position is rotatably oriented at least a predetermined angular position from the first position. Preferably, the second position is oriented at least about 90° from the first position. The second drive means includes rack gear means secured to a second drive member and adapted for engagement with the gear means such that linear movement of the rack gear means causes rotational movement of the die cartridge.

The apparatus also includes needle gripping means for maintaining the needle in a predetermined position when the die means is actuated. In addition, the apparatus of the present invention may further include guide means positioned adjacent the die means for guiding the suture into a bore in the end face of the needle. The guide means is adjustable in at least two directions, preferably, horizontal and vertical.

Control means is provided and operatively connected to the first and second drive means for selectively activating the first and second drive means. Generally, the control means includes pneumatic and electrical controls and switch means for automatically terminating the impacting and the rotation of the die means.

The present invention also relates to a method for attaching surgical suture components which includes releasably securing a surgical needle having a bore in an end face between a pair of dies, orienting the dies and the needle to a first position, inserting a surgical suture into the needle bore, impacting the needle with the pair of dies so as to secure the suture to the needle, rotating the pair of dies a predetermined rotational amount until the dies are oriented at an angle relative to the first orientation, and impacting the needle with the pair of dies so as to further secure the suture to the needle.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
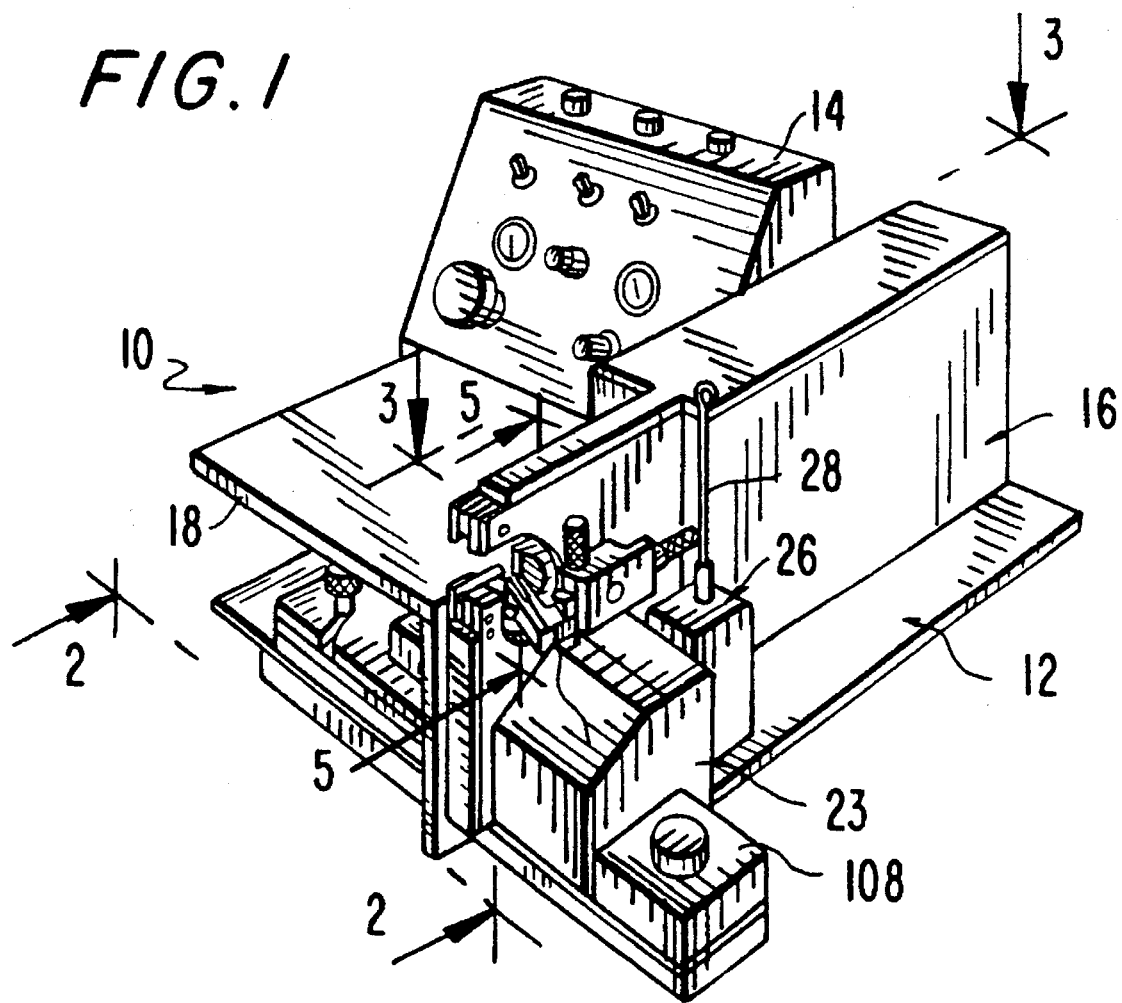
FIG. 1 is a perspective view of the suture needle attaching apparatus of the present invention.

Referring initially to FIG. 1, the apparatus 10 generally includes frame 12 to support the various components of the apparatus, control panel 14 and die rotating and crimping system 16. Control panel 14 may be secured to, or independent of frame 12 and provides electrical and pneumatic controls for the active components of apparatus 10. The electrical and pneumatic controls and devices for control panel 14 are preferably of a type known in the art and include, for example, electrical and pneumatic switches, air pressure gauges and light indicators. Die rotating and crimping system 16 is secured to frame 12 as shown and is provided to rotate and crimp the crimping dies.

Figure 2:
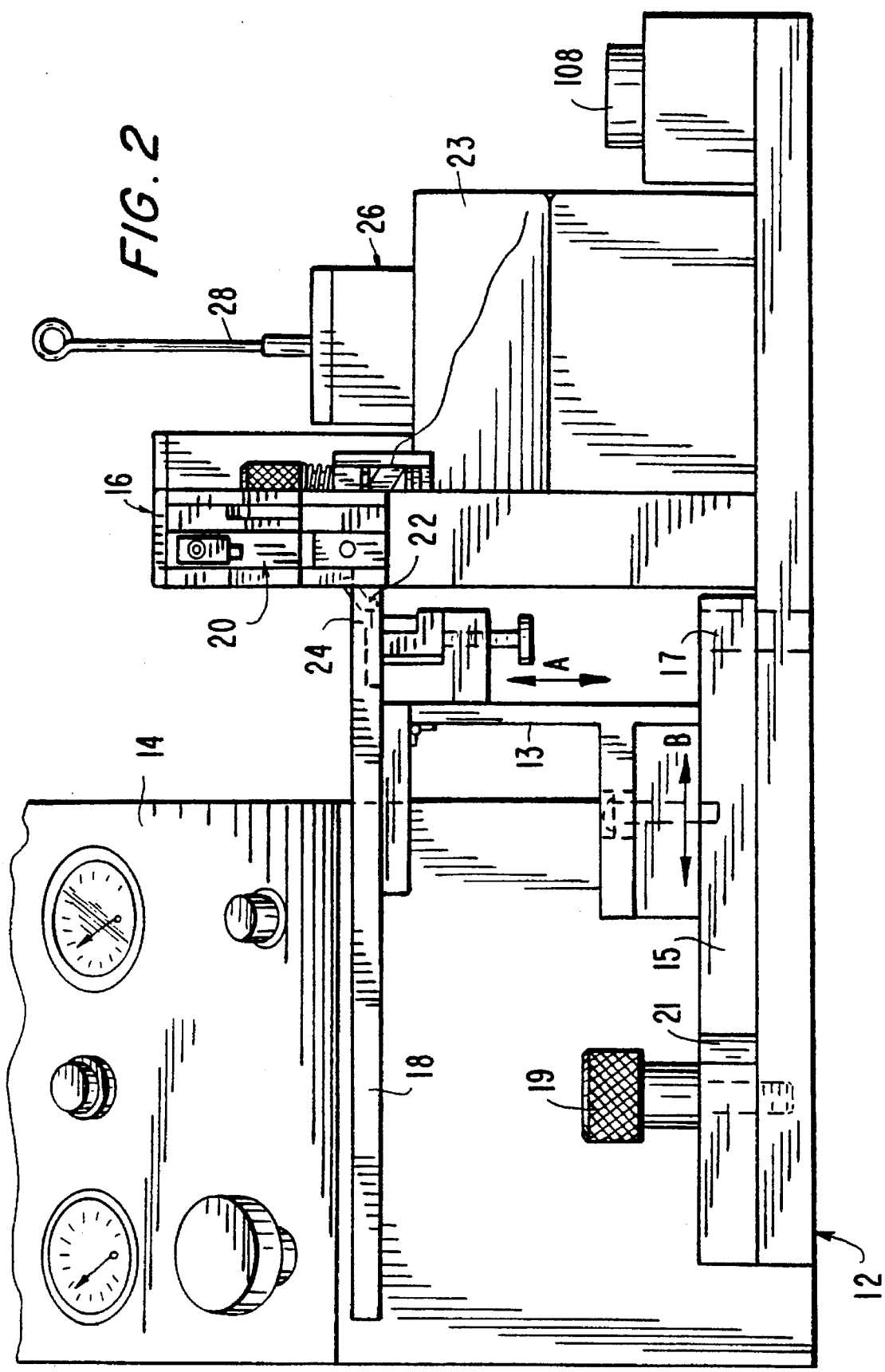
FIG. 2 is a front elevational view of the suture needle attaching apparatus taken along lines 2—2 of FIG. 1.
Figure 3:
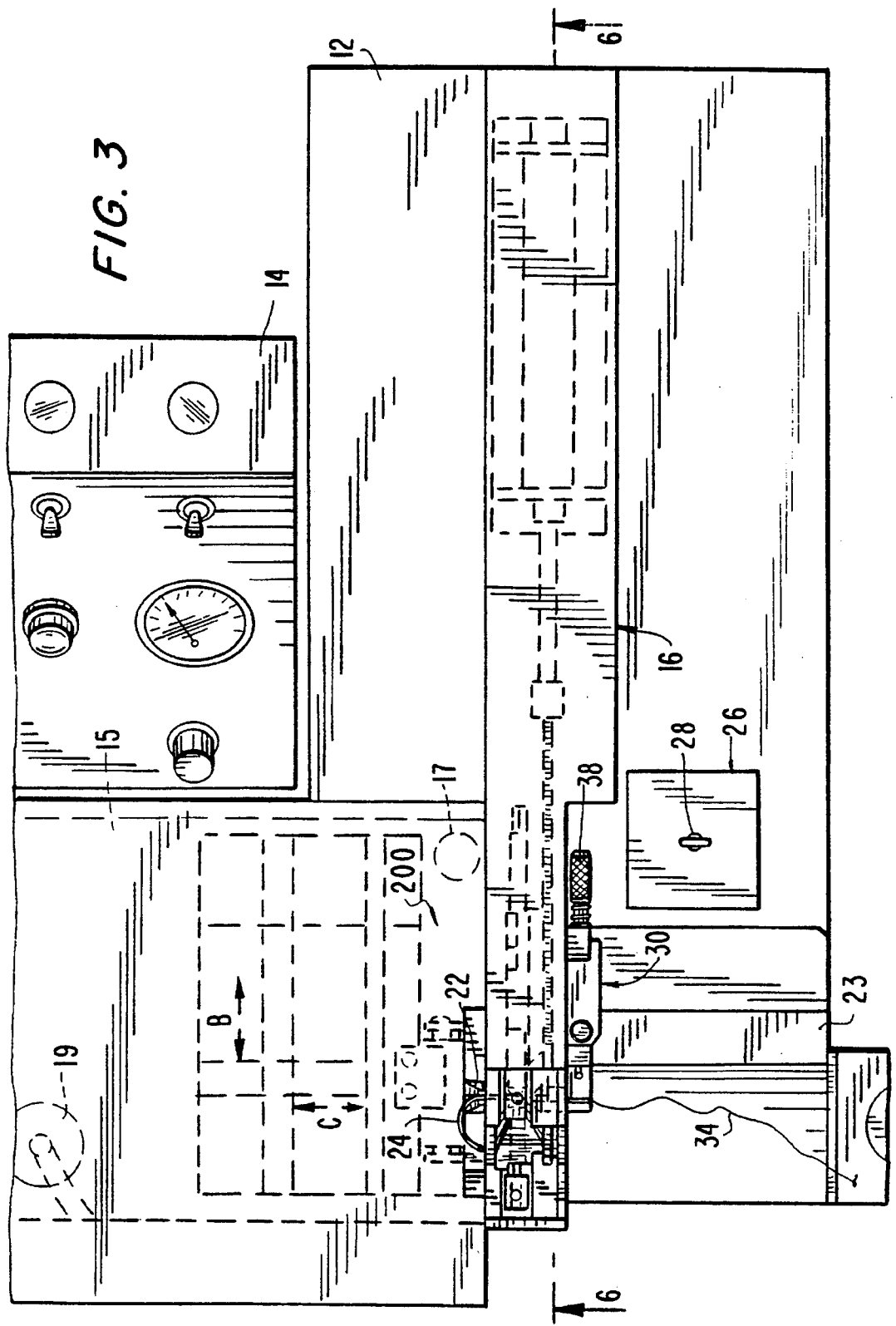
FIG. 3 is a top plan view of the suture needle attaching apparatus taken along line 3—3 of FIG. 1.
Figure 4:
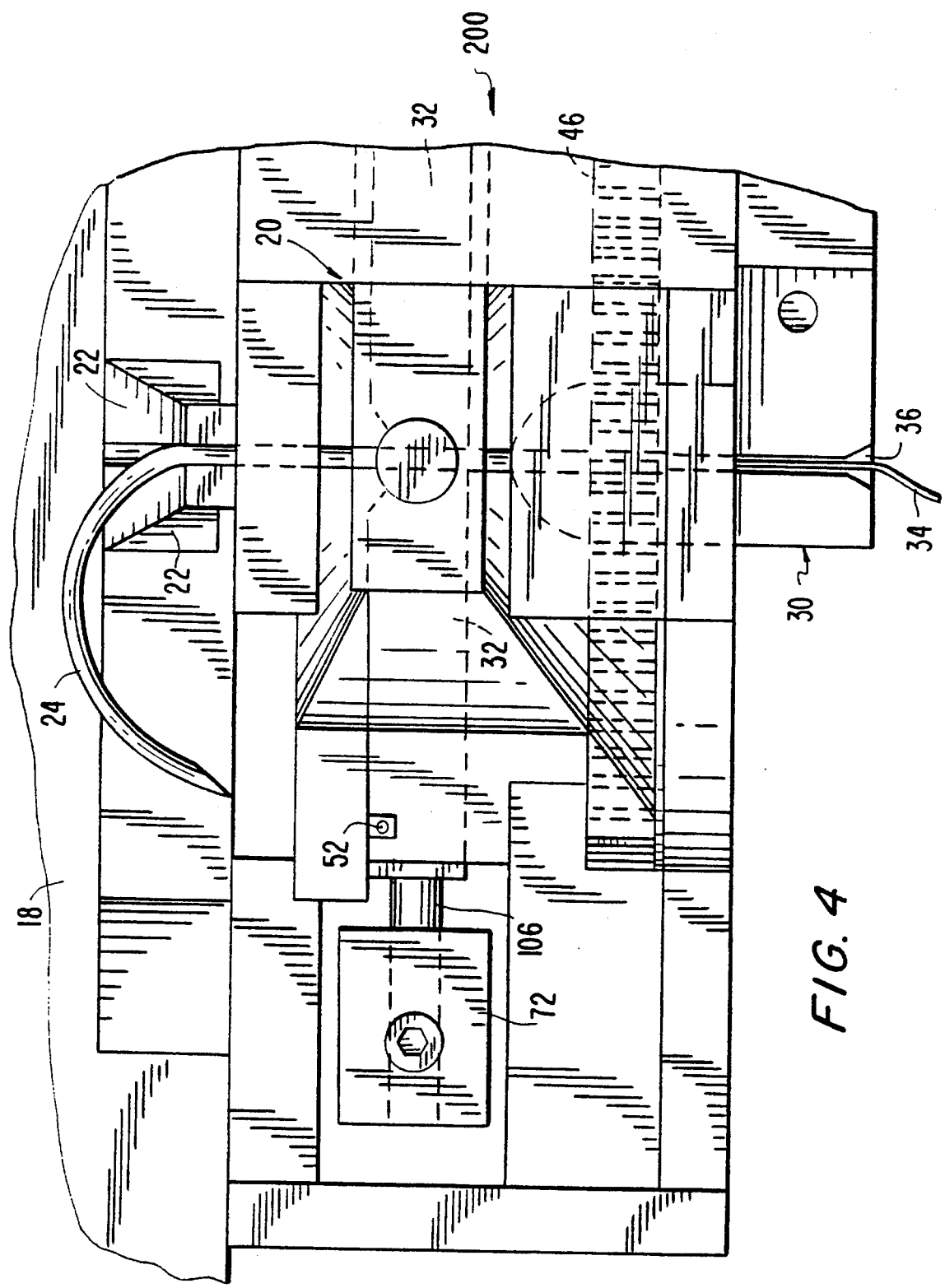
FIG. 4 is an enlarged top plan view of the crimping zone of the apparatus of FIG. 1.

Referring now to FIGS. 2–4, frame 12 further includes horizontal support table 18 which is provided to support the needle 24 and is adjustable in three directions of a three-dimensional coordinate system, as shown by arrows A, B and C. For example, as viewed in FIG. 1, direction "A" represents vertical movement, direction "B" represents fore and aft movement and direction "C" represents lateral (i.e., left and right) movement.

Referring once again to FIGS. 2–4, table 18 rests on vertical bracket 13 and the bracket rests on support base 15. Support base 15 is pivotally mounted to frame 12 by pivot pin 17 to provide pivotal movement of table 18, bracket 13 and support base 15. Thumb screw 19 secures support base 15 to frame 12 so that table 18 is maintained in a fixed relation to the frame. Loosening of thumb screw 19 permits free pivotal movement of table 18 with respect to frame 12. Such pivotal movement permits access to the die rotating and crimping system 16 to facilitate ease of removal or insertion of die cartridge 20 into the die rotating and crimping system 16. Needle grippers 22, best shown in FIG. 4, are secured to table 18, adjacent die cartridge 20 so that when needle 24 is positioned between needle grippers 22 the needle will automatically become aligned with the working surface of the crimping dies as shown in crimping area 200 of FIGS. 3 and 4. Preferably, needle grippers 22 are pneumatic jaws controlled by control panel 14 as will be described in further detail below. Hand rest 23 is secured to frame 12 adjacent die cartridge 20 and provides the operator with an ergonomic hand rest when inserting sutures into the needle and when operating the apparatus of the present invention.

Referring again to FIG. 1, emergency stop switch 26 is secured to frame 12 and is provided to terminate the power to the active components of the apparatus and prevent further actuation thereof. Preferably, emergency stop switch 26 is positioned in close proximity to die cartridge 20, as shown in FIG. 1, so as to enable the operator to quickly move arm 28 of emergency switch 26 with fingers to shut down of the system in the event of an emergency.

Figure 5:
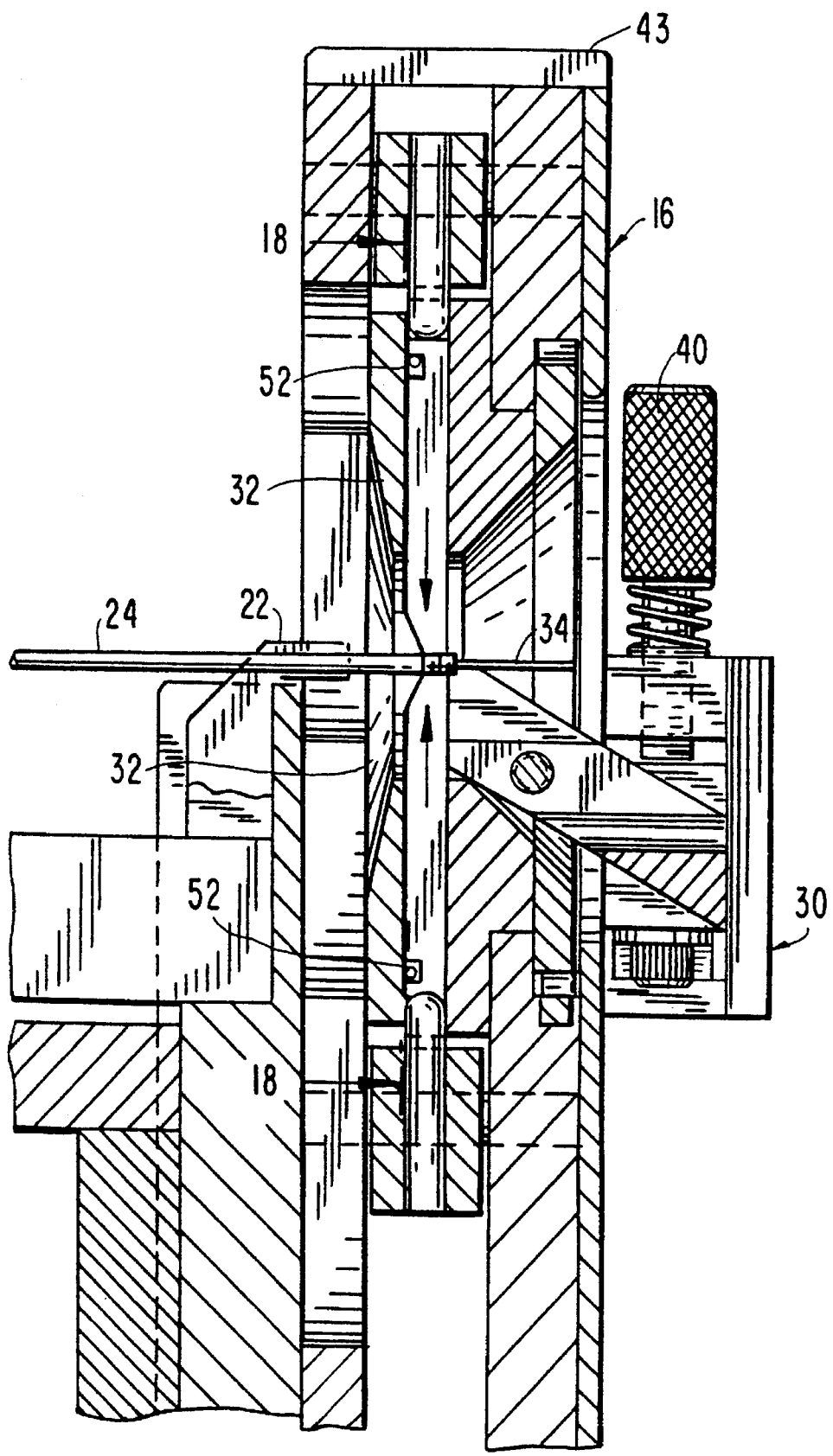
FIG. 5 is a front elevational view of the suture needle attaching apparatus taken along lines 5—5 of FIG. 1, illustrating the dies rotated 90° and the needle positioned for crimping.

Referring now to FIGS. 4 and 5, enlarged views of the needle crimping zone are illustrated. Guide member 30 is secured to die rotating and crimping system 16 adjacent die cartridge 20 to perform two functions. First, guide member 30 includes channel 36, shown in FIG. 4, to guide suture 34 into an appropriately dimensioned opening in the end face of needle 24. Second, guide member 30 is a stop member which limits the positioning of needle 24 between dies 32 so that the dies crimp the needle at a point where suture 34 will be engaged or crimped by the deformed surface of the needle. Preferably, guide member 30 is adjustable in the horizontal direction via adjusting screw 38, shown in FIG. 3, and the vertical direction via adjusting screw 40, shown in FIG. 5.

Figure 6:
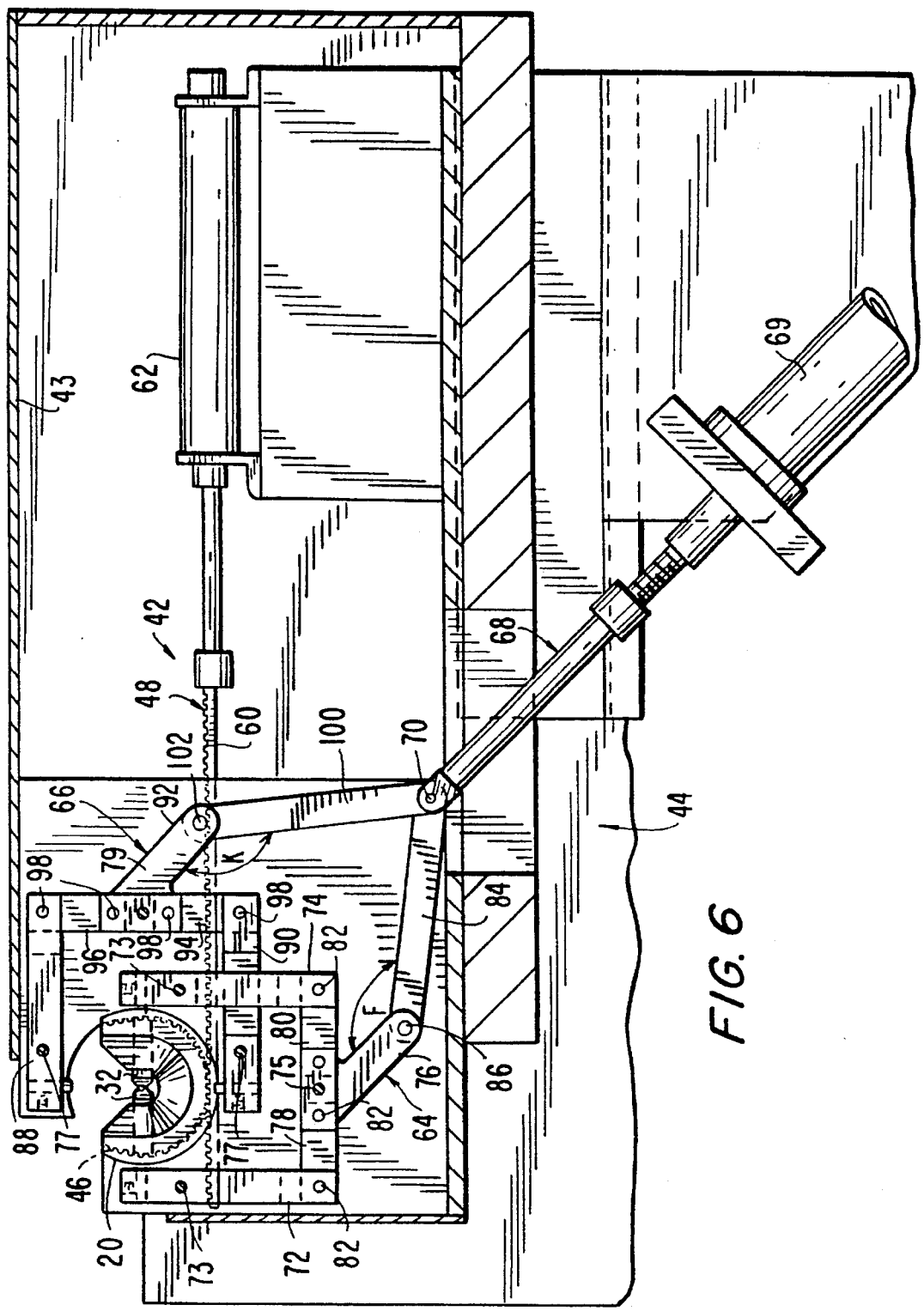
FIG. 6 is a side elevational view of the rotating and crimping system associated with the suture needle attaching apparatus of the present invention.
Figure 7:
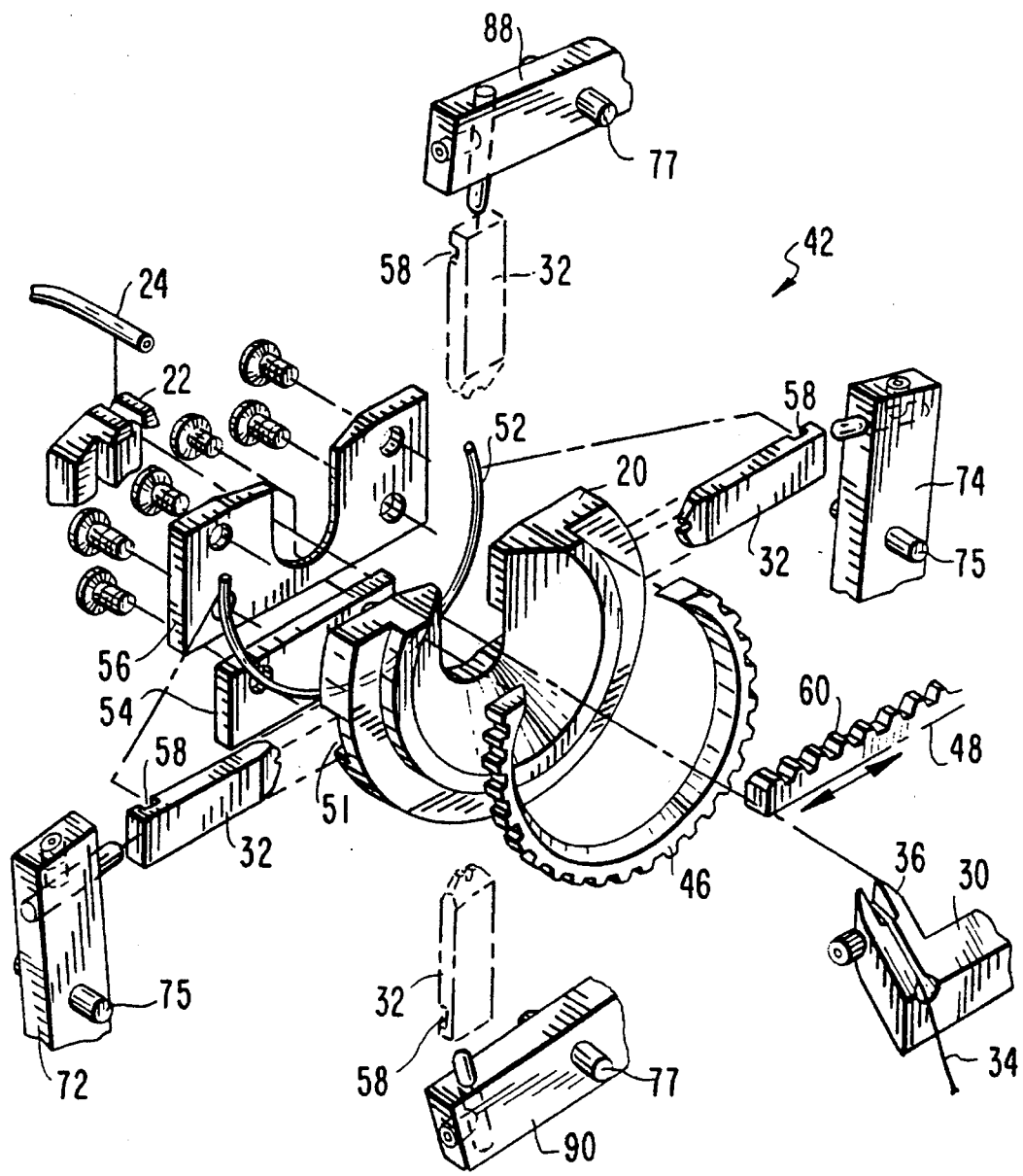
FIG. 7 is an enlarged perspective view with parts separated of a portion of the rotating and crimping systems of FIG. 6.
Figure 8:
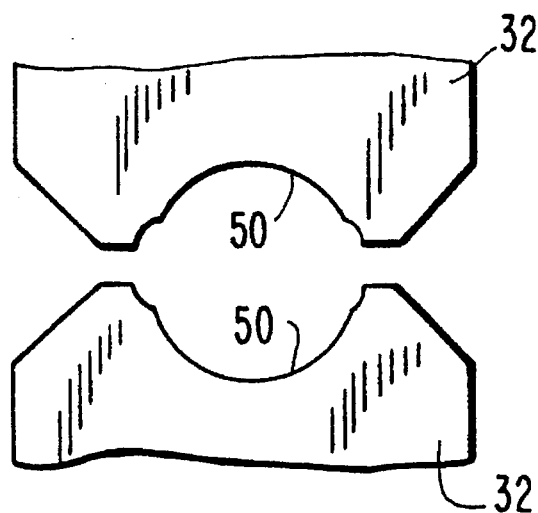
FIG. 8 is a plan view of a portion of the dies of the crimping system of FIG. 6, illustrating a "lap-overlap" die configuration.
Figure 9:
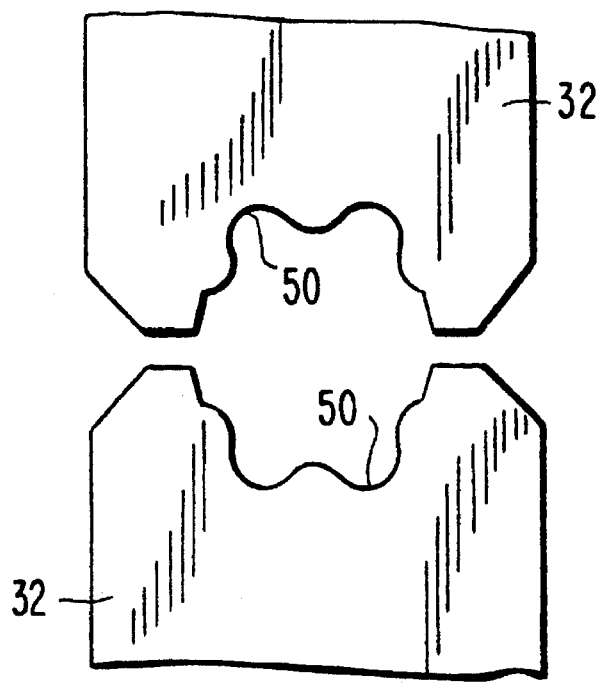
FIG. 9 is a plan view of a portion of an alternative embodiment of the crimping system of FIG. 6, illustrating a "clover leaf" die configuration.

Referring now to FIGS. 6–9, the rotating and crimping system 16 of the present invention will now be described. Rotating and crimping system 16 includes a rotating portion 42 and a crimping portion 44, both of which are positioned within housing 43, as shown in FIG. 6. As shown in FIGS. 6 and 7, rotating portion 42 generally includes a pair of needle crimping dies 32, rotating die cartridge or member 20, pinion gear 46 secured to die cartridge 20 and rack gear 48 which engages pinion gear 46 so as to translate linear movement of rack gear 48 to rotational movement of die cartridge 20. The working surface 50 of each die 32 is preferably the "lap-overlap" type, shown in FIG. 8. However, the working surface 50 of each die may be of the "clover leaf" type, shown in FIG. 9, the staking type (not shown) or the like. One example of a clover leaf die of this type is described in commonly assigned U.S. Pat. No. 5,099,676 to Proto et al. Another example of a preferred die configuration is illustrated in U.S. Pat. No. 5,046,350 to Proto et al.

Figure 10:
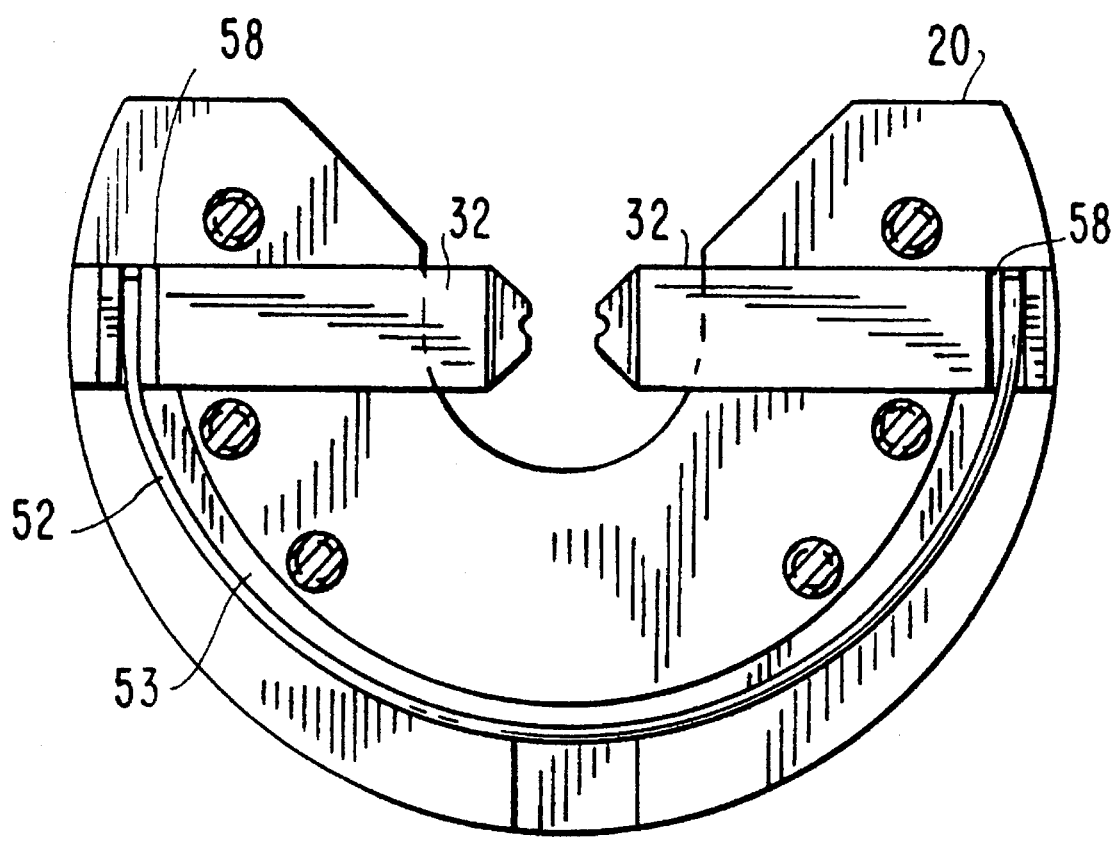
FIG. 10 is a side elevational view of a portion of the die cartridge shown in FIG. 7, illustrating the sliding relationship between the die cartridge and the dies.

Referring again to FIGS. 6–7, dies 32 are positioned on die cartridge 20 such that the working surface 50 of each die 32 oppose each other and at least one of the dies is slidably secured thereto. Preferably, both dies are positioned within channels 51 in the form of die cartridge 20 and are slidably retained therein, as shown in FIG. 7. Arcuate spring 52 in the form of a large circlip as shown, is positioned within arcuate channel 53 of die cartridge 20 so that each end portion of arcuate spring 52 engages a corresponding die channel 58 in each die 32, as shown in FIG. 10. The dies 32 and arcuate spring 52 are then secured to die cartridge 20 by removable plates 54 and 56. In this configuration, spring 52 normally biases dies 32 in directions away from the center of die cartridge 20.

Referring to FIG. 6, rotating portion 42 is shown. Rack gear 48 includes gear section 60 attached to linear drive section 62. Gear section 60 of rack gear 48 is configured to engage pinion gear 46, as mentioned above. Preferably, linear drive section 62 is a pneumatic pump which is controlled by control panel 14, as will be discussed hereinbelow. However, drive section 50 may be any known drive system, such as an electric motor or hydraulic pump.

Continuing to refer to FIG. 6, the crimping portion 44 will now be described. Crimping portion 44 includes a pair of crimping arms 64 and 66 which are pivotally secured to crimping drive member 68 by pin 70. Each crimping arm is substantially identical and provided to selectively cause dies 32 to bias toward the center of die cartridge 20. Crimping arm 64 includes a pair of lever arms 72 and 74 which are pivotally connected to pivot arm 76 via cross-bars 78 and 80 and pins 82. In addition, securing pins 73, positioned on the upper portion of lever arms 72 and 74, and securing pin 75 positioned on pivot arm 76 are provided to maintain lever arms 72 and 74 in a fixed pivotal relationship within housing 43 so that lever arms 72 and 74 and cross bars 78 and 80 form a "U" shaped chamber to partially receive die cartridge 20, as shown in FIG. 6. Pivot arm 76 is also pivotally secured to articulating arm 84 by pin 86, and articulating arm 84 is secured to crimping drive member 68 by pin 70.

Similarly, crimping arm 66 includes a pair of lever arms 88 and 90 which are pivotally connected to pivot arm 92 via cross-bars 94 and 96 and pins 98. In addition, securing pins 77, positioned on the upper portion of lever arms 88 and 90, and securing pin 79 positioned on pivot arm 92 are provided to maintain lever arms 88 and 90 in a fixed pivotal relationship within housing 43 so that lever arms 88 and 90 and cross-bars 94 and 96 form a "U" shaped chamber to partially receive die cartridge 20, as shown in FIG. 6.

Preferably, lever arms 88 and 90 are positioned about the die cartridge 90° out of phase from lever arms 72 and 74 as shown. This configuration provides uniform crimping of suture 34 to needle 24. Pivot arm 92 is also pivotally secured to articulating arm 100 by pin 102 and articulating arm 100 is pivotally secured to crimping drive member 68 by pin 70. Also, preferably, crimping drive member 68 is connected to a pneumatic pump 69 as shown, which is operator controlled at control panel 14, as will be discussed below. However, crimping drive member 68 may be connected to any other known type of drive system, such as an electric motor or a hydraulic pump, etc.

The operation of the apparatus of the present invention will now be described with particular reference to FIGS. 11–20 in conjunction with FIGS. 1–6. Generally, when the dies are in the crimping position pneumatic pump 69 causes crimping drive member 68 to be located at the center of its stroke. When the dies are in the open position crimping drive member 68 is at either the extended or retracted end of its stroke as determined by pneumatic pump 69.

Figure 11:
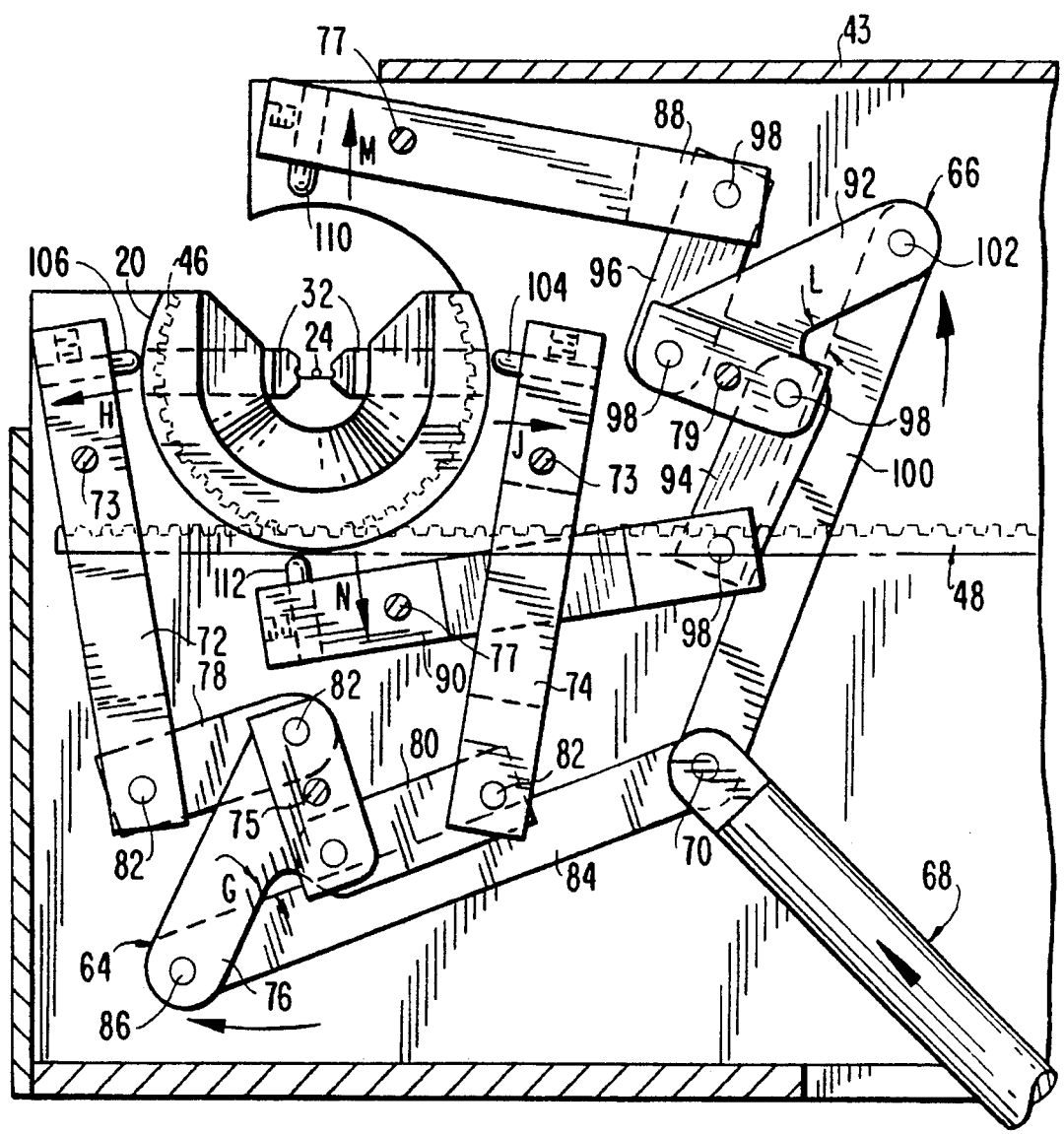
FIG. 11 is a side elevational view of a portion of the rotating and crimping systems of FIG. 6, illustrating the die cartridge in a normal position and the dies in an open position.

Referring now to FIG. 11, initially die cartridge 20 is positioned in the normal position, i.e., crimping drive member 68 is at the extended end of the stroke and dies 32 are in the open position and horizontally orientated as shown. However, depending upon the desired sequence, crimping drive member 68 could initially be at the retracted end of the stroke when in the normal position. As mentioned above, securing pins 73, 75, 77 and 79 maintain each corresponding pair of lever arms in a fixed pivotal relationship within housing 43, thus, when the stroke of crimping drive member 68 moves toward the extended end, shown by arrow E, articulating arm 84 pivots causing pivotal movement of pivot arm 76 about securing pin 75 via pin 86. As a result, obtuse angle "F", shown in FIG. 6, is decreased to acute angle "G", shown in FIG. 11 The described pivotal motion of pivot arm 76 causes lever arms 72 and 74 to pivot away from the center of die cartridge 20, shown by arrows "H" and "J", in response to pivotal movement of cross bars 78 and 80. Similarly, articulating arm 100 pivots in response to the above described motion of crimping drive member 68, causing pivot arm 92 to pivot about securing pin 79 via pin 102. As a result, obtuse angle K, shown in FIG. 6, is decreased to acute angle L, shown in FIG. 11. The described pivotal motion of pivot arm 92 causes lever arms 88 and 90 to pivot away from the center of die cartridge 20, shown by arrows M and N, in response to pivotal movement of cross-bars 94 and 96. As a result of the movement by lever arms 72 and 74 away from the center of die cartridge 20, pusher pins 104 and 106 disengage dies 32 so as to allow dies 32 to bias towards their normal position in response to arcuate spring 52, as noted above.

Figure 12:
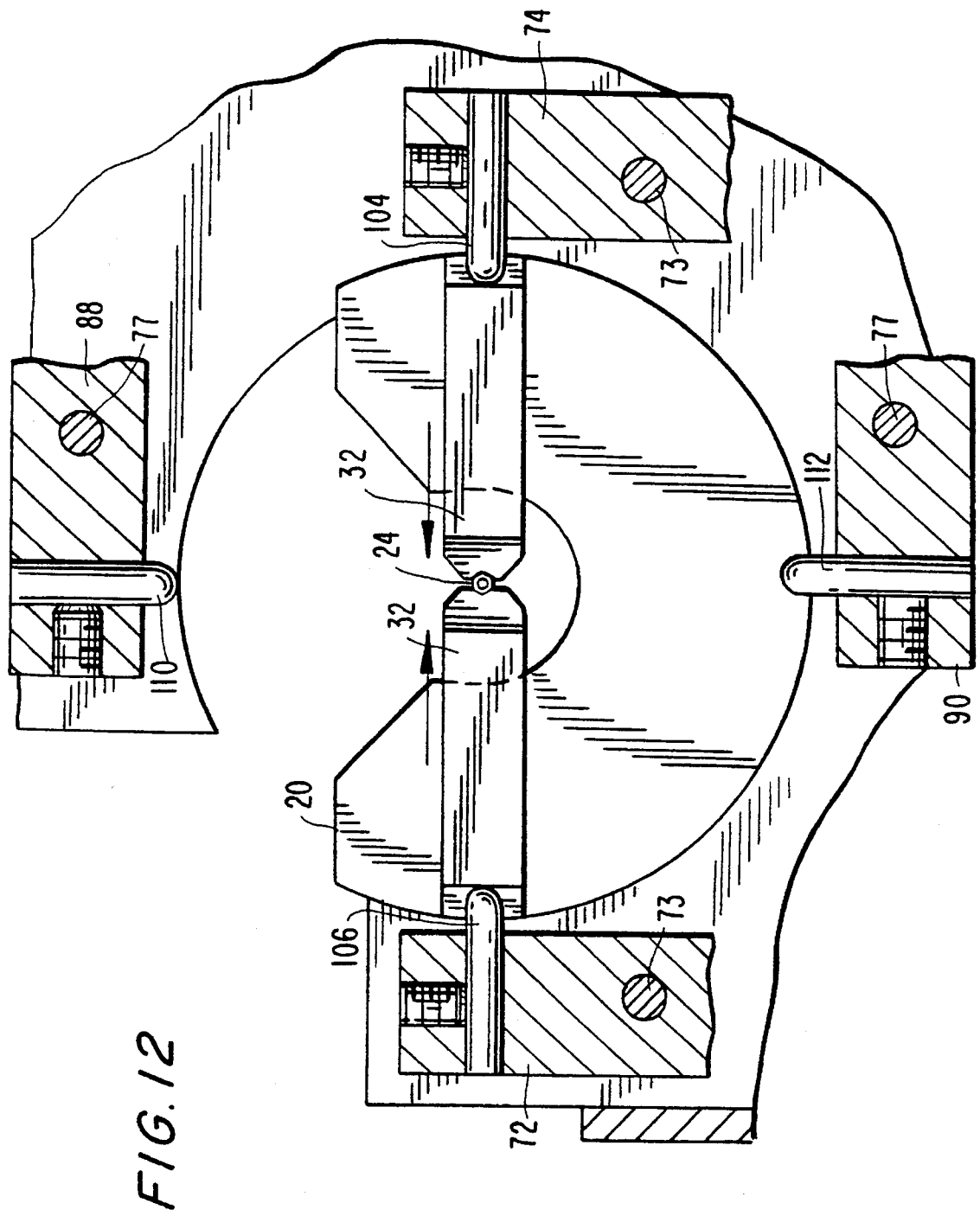
FIG. 12 is a side elevational view, greatly enlarged, of the die cartridge of FIG. 11, illustrating the dies in a preset position.

When dies 32 are in the open position, the operator inserts a needle 24 between dies 32 until the needle face abuts guide member 30, as shown in FIG. 5. The operator then activates control panel 14 so that dies 32 and needle grippers 22 are respectively set to a preset position. To activate control panel 14, a center pivot foot pedal (not shown) may be utilized which will set dies 32 and needle grippers 22 to the preset position when tilted in one direction and activate the crimping cycle when tilted in the other direction. As shown in FIG. 12, the preset position is the position where dies 32 grasp needle 24 with a force, exerted by pusher pins 104 and 106, sufficient to maintain needle 24 therebetween without substantially deforming the needle. The preferred force is about 10 psi. Either simultaneously with the preset gripping by dies 32 or after a time delay of approximately two seconds, needle grippers 22 also grasp needle 24 to maintain the position of the needle during the crimping cycle of the apparatus, as shown in FIGS. 3 and 4. Reset switch 108 is provided to allow the operator to reset the crimping system from the preset position by causing control panel 14 to open dies 32 and needle grippers 22 via crimping portion 44. Once in the preset position, a suture 34 is inserted into the needle bore via guide member 30, as described above.

Figure 13:
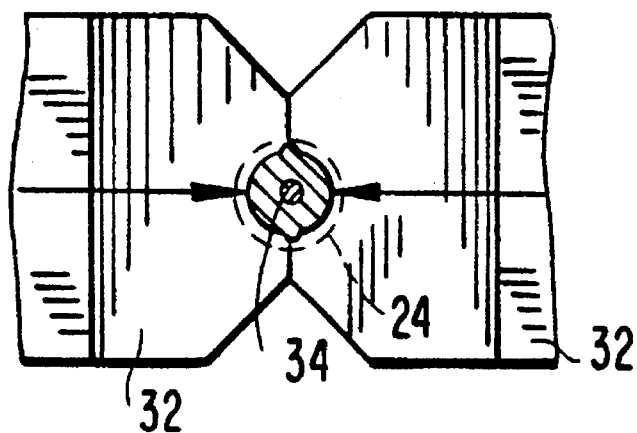
FIG. 13 is a plan view of the dies of FIG. 8 in the normal position and having a crimped needle positioned therebetween.
Figure 14:
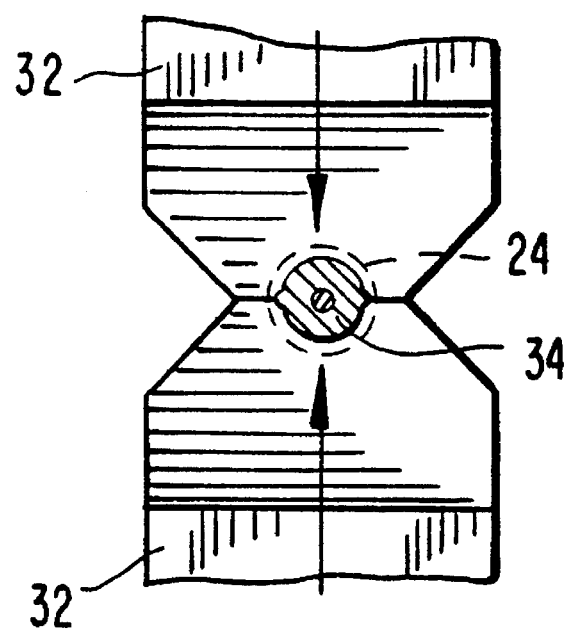
FIG. 14 is a plan view of the dies of FIG. 13, illustrating the dies in a rotated position and the needle crimped therebetween.

After insertion of suture 34 the crimping cycle is activated by control panel 14. As mentioned above, the foot pedal is preferably utilized to activate the crimping cycle. Generally, the crimping cycle includes two steps. The first step crimps the needle on two sides and the second step rotates the dies and crimps the needle on two sides which are out of phase with the sides originally crimped, as shown in FIGS. 13 and 14. Preferably, the second crimping action is 90° out of phase with the first crimping action to ensure a uniform attachment of the suture to the needle. It should be noted that for each part of the crimping cycle the dies are caused to impact the needle twice so as to ensure sufficient and uniform crimping of the suture within the needle bore.

Figure 15:
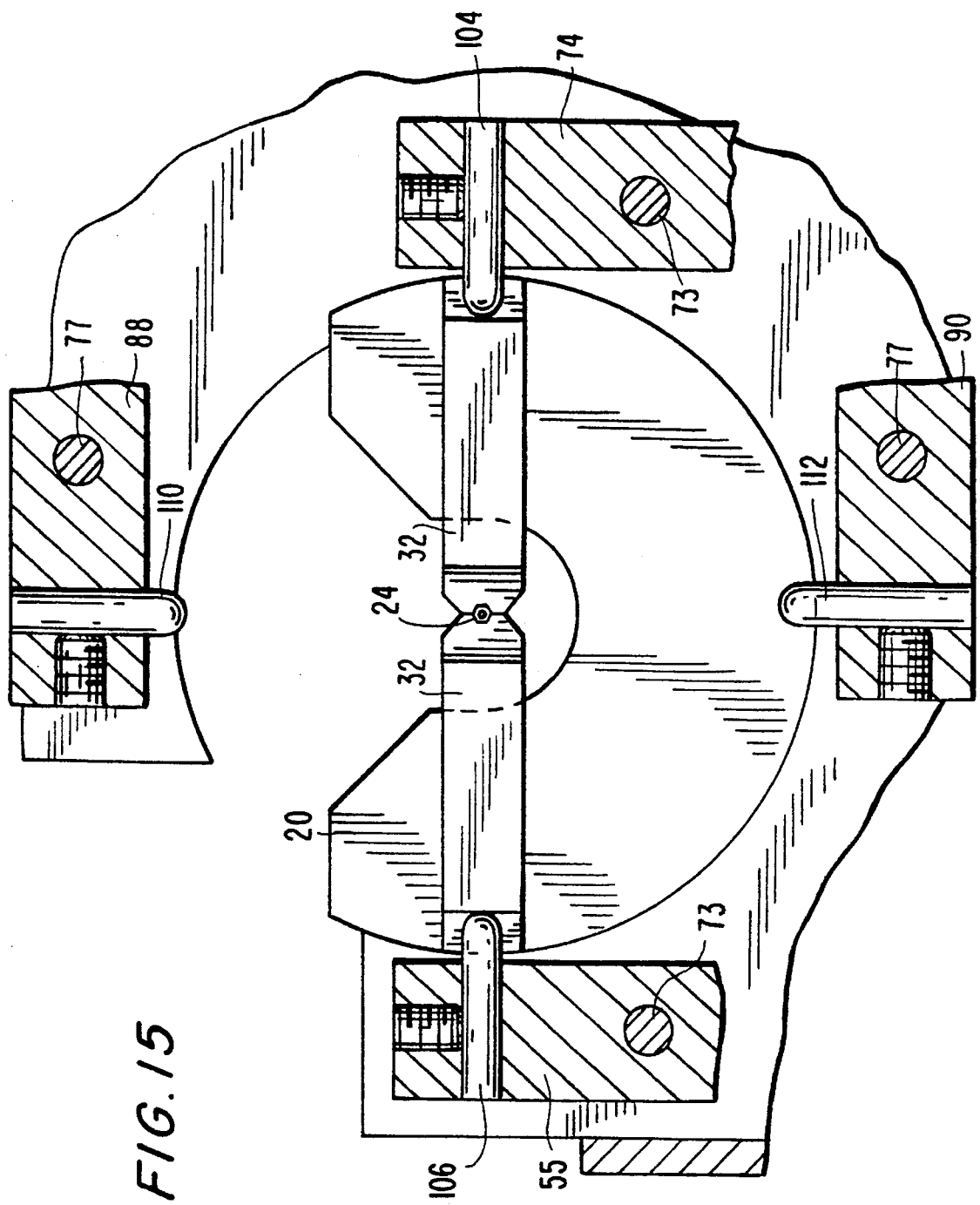
FIG. 15 is a side elevational view, greatly enlarged, of the die cartridge of FIG. 11, illustrating the dies in a crimping position.

Referring to FIGS. 11 and 15, the first step of the crimping cycle causes crimping drive member 68 to move towards the center of the stroke so that pusher pins 104 and 106 bias dies 32 towards needle 24 sufficiently to deform the needle surface with the working surface of each die and secure suture 34 thereto. Preferably, the force applied to deform needle 24 by pusher pins 104 and 106 is about 85 psi. After deforming the needle surface, the dies are caused to return to the open position shown in FIG. 11 by moving crimping drive member to either the extended or retracted end of the stroke as described above.

Once the first part of the crimping cycle is completed the apparatus automatically rotates die cartridge 20 so that each die 32 is shifted a predetermined distance from their normal position, preferably about 90°. As previously mentioned, rotational movement of die cartridge 20 occurs when linear drive section 62, shown in FIG. 6, retracts gear section 68, shown by arrow P in FIG. 16.

Figure 16:
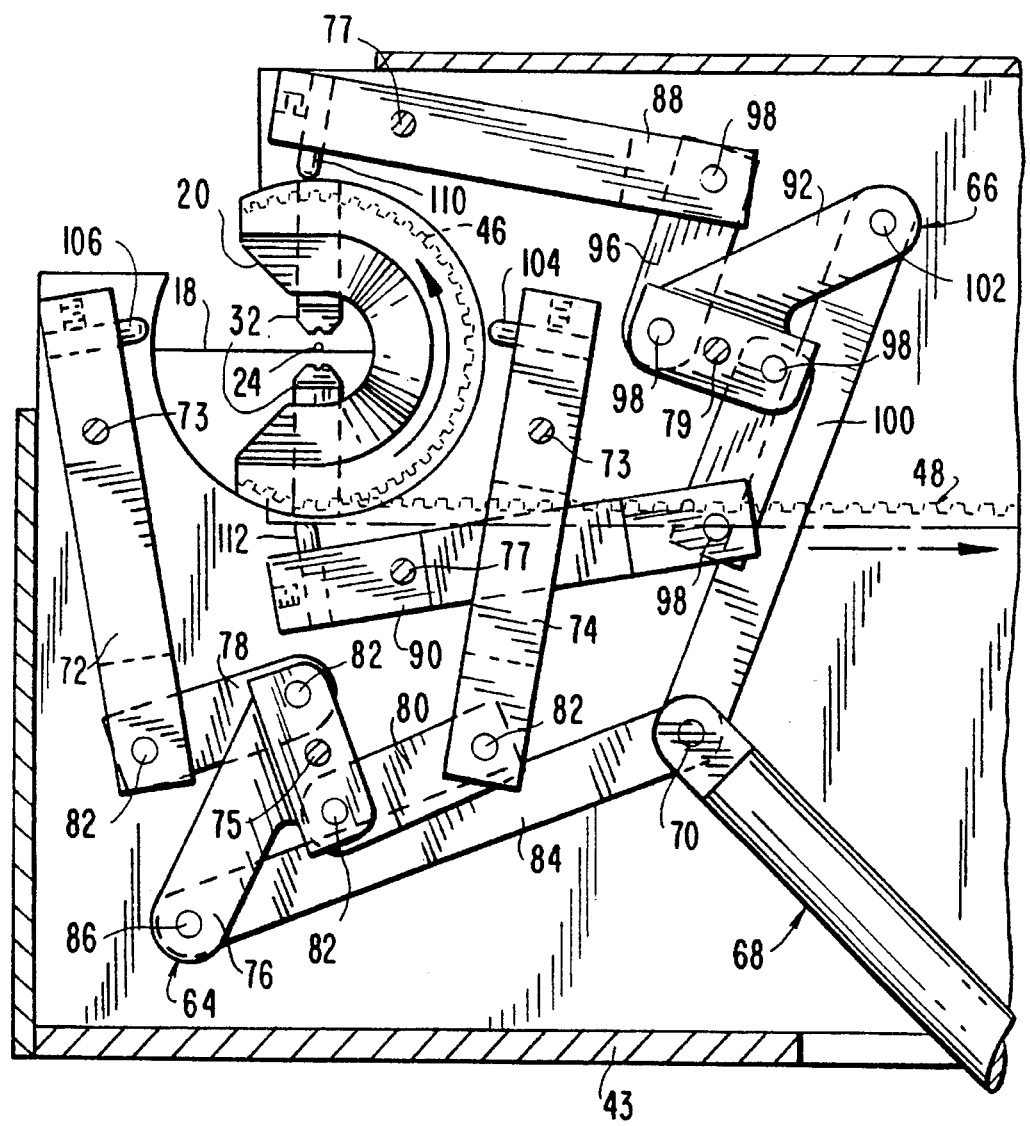
FIG. 16 is a side elevational view similar to FIG. 11, of the rotating and crimping system, illustrating the die cartridge in a rotated position and the dies in an open position.
Figure 17:
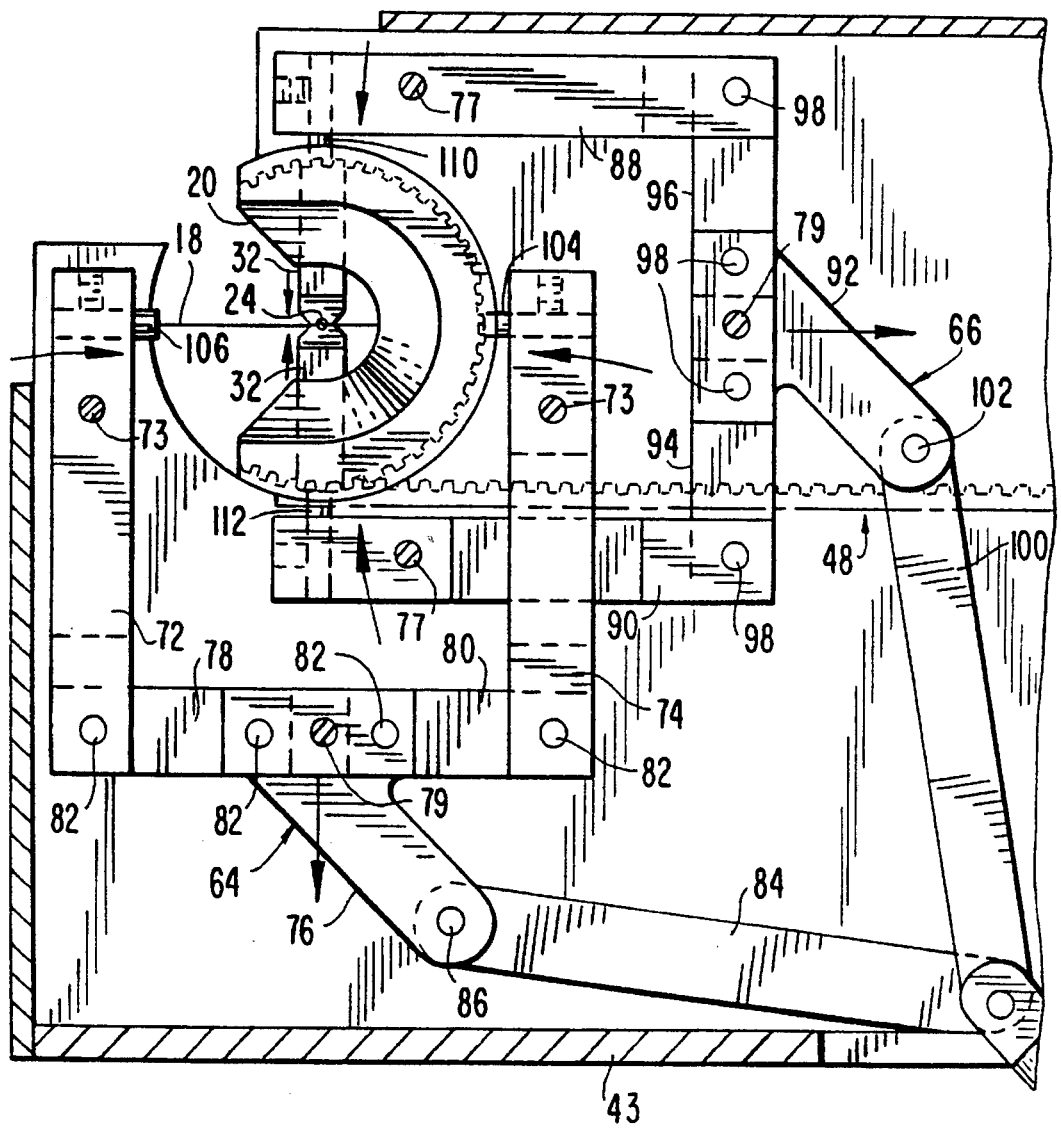
FIG. 17 is a side elevational view of the rotating and crimping systems of FIG. 16, illustrating the dies in a crimping position.
Figure 18:
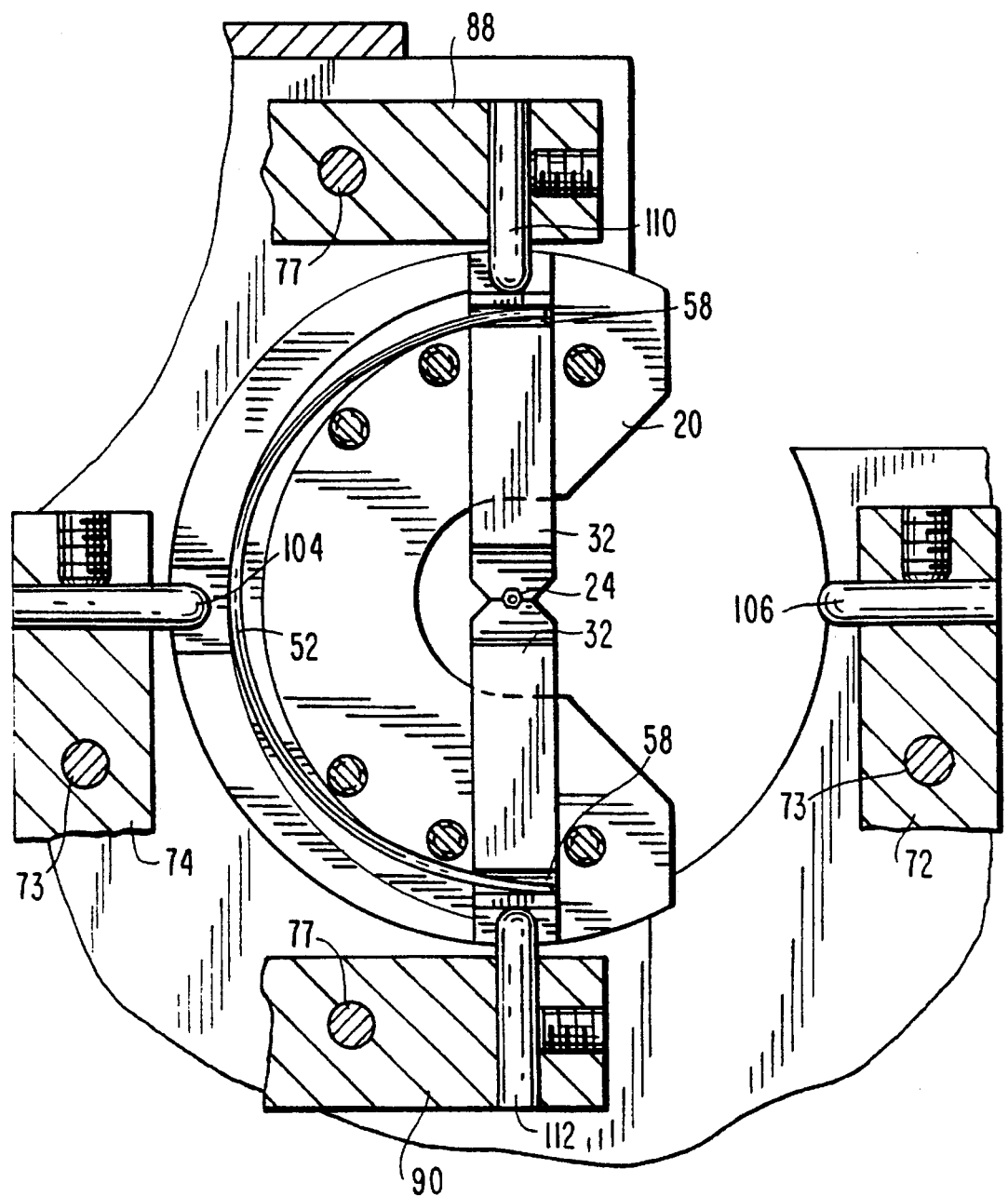
FIG. 18 is a side elevational view of the die cartridge taken along lines 18—18 of FIG. 5 illustrating the dies in a crimped position.
Figure 19:
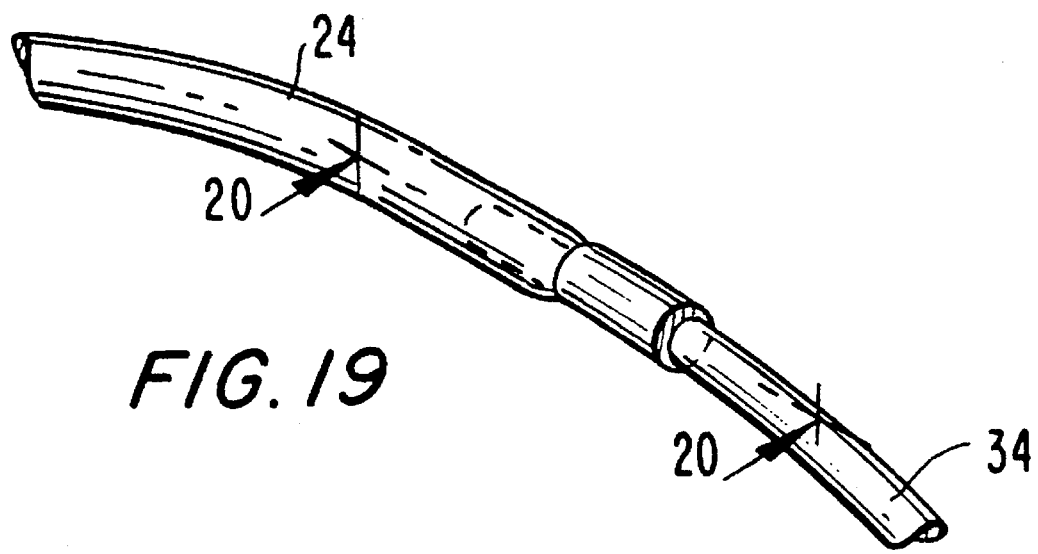
FIG. 19 is a perspective view of a portion of a surgical suture crimped to a surgical needle.
Figure 20:
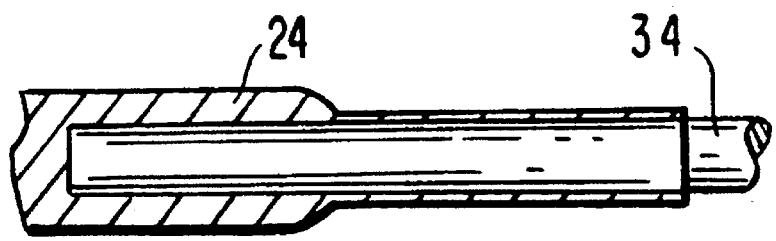
FIG. 20 is a partial cross-sectional view of the crimped surgical suture taken along lines 20—20 of FIG. 19.

Referring now to FIGS. 17 and 18, after rotating die cartridge 20, crimping portion 44 is again activated so that pusher pins 110 and 112 bias dies 32 towards needle 24 sufficiently to deform the needle surface with the working surface of each die 32 thus, securing suture 34 to needle 24 in a uniform manner. As mentioned above, it is preferred that for each part of the crimping cycle the needle and suture are impacted twice. After completing the second part of the crimp cycle the dies are again opened by causing crimping drive member 68 to extend or retract to the end of the stroke, as shown in FIG. 16. Once the dies are opened the operator may remove the crimped needle and suture, shown in FIGS. 19 and 20.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. Apparatus for attaching a surgical suture to an eyeless needle comprising:

support means;

die means attached to said support means for selectively impacting the needle such that a portion of the needle is deformed to maintain the suture therein, said die means being reciprocally rotatable between at least two positions;

first drive means associated with said support means for actuating said die means to impact the needle;

second drive means associated with said support means for reciprocally rotating said die means between said at least two positions relative to said needle; and guide means positioned adjacent said die means for guiding the suture into a bore in the end face of the needle, said guide means being adjustable in at least two directions.

2. The apparatus according to claim 1, wherein said guide means includes a pair of arms, wherein at least one of said pair of arms has a suture guiding channel which guides the suture into the bore in the end face of the needle, and wherein at least one of said pair of arms is movable relative to the other to facilitate removal of the suture from the channel after the suture is attached to the needle.

3. Apparatus for attaching a surgical suture to an eyeless needle comprising:

a die cartridge having at least one jaw slidably secured thereto configured to selectively impact the needle such that a portion of the needle is deformed to maintain the suture therein, said die cartridge positioned at least partially within a housing and configured to alternately move in opposite directions between at least two positions relative to said housing;

a jaw drive member operatively associated with said die cartridge and configured to move said at least one jaw to impact the needle in at least one of said at least two positions; and a cartridge drive member operatively connected to said die cartridge such that upon actuation of said cartridge drive member said die cartridge alternately moves between said at least two positions relative to the needle.

4. The apparatus according to claim 3 further comprising a needle gripping member positioned adjacent said housing and configured to maintain the needle in a fixed position relative to said die cartridge at least when said at least one jaw is moved by said jaw drive member.

5. The apparatus according to claim 3 further comprising a suture guide member positioned adjacent said die cartridge to guide a suture into a bore in the end face of the needle.

6. The apparatus according to claim 5, wherein said suture guide member includes a pair of arms, said arms defining a suture guiding channel which guides the suture into the bore in the end face of the needle, and wherein at least one of said pair of arms is movable relative to the other such that subsequent to impacting of the needle by said at least one jaw, said at least one arm may be displaced from the other arm to define an opening to facilitate removal of the suture from the channel.

7. The apparatus according to claim 6, wherein each said pair of arms includes a groove which when positioned adjacent one another define said suture guiding channel.

8. The apparatus according to claim 3, wherein said die cartridge is alternately movable between first and second positions, wherein said second position is oriented at a predetermined angular position from said first position.

9. The apparatus according to claim 8, wherein said predetermined angular position is about 90°.

10. The apparatus according to claim 8, wherein said jaw drive member moves said at least one jaw to impact the needle when said die cartridge is in said first and second positions.

11. The apparatus according to claim 3, wherein said die cartridge includes a pair of jaws each having a working surface, said pair of jaws being slidable relative to each other such that said working surfaces impact the needle in response to actuation of said jaw drive member.

12. Apparatus for attaching a surgical suture to an eyeless needle comprising:

a frame;

a needle impacting mechanism attached to said frame and reciprocally rotatable between at least two positions relative to said frame, said needle impacting mechanism being configured to selectively impact the needle such that a portion of the needle is deformed to maintain the suture therein;

a first drive member operatively connected to said needle impacting mechanism such that actuation of said first drive member causes said needle impacting mechanism to impact the needle;

a second drive member operatively connected to said needle impacting mechanism and configured to reciprocally rotate said needle impacting mechanism between said at least two positions; and a suture guide positioned adjacent said needle impacting mechanism to guide the suture into a bore in the end face of the needle.

13. The apparatus according to claim 12, wherein said needle impacting mechanism comprises at least one pair of dies secured to a die housing, said at least one pair of dies being movable between impacting and non-impacting positions.

14. The apparatus according to claim 13, wherein actuation of said first drive member moves said at least one pair of dies between said impacting and non-impacting positions.

15. The apparatus according to claim 13, wherein actuation of said second drive member rotates said die housing between said at least two positions.

16. The apparatus according to claim 13, wherein said at least one pair of dies impacts the needle when in said at least two positions.

17. The apparatus according to claim 13, wherein said die housing is alternately rotatable between first and second positions, said second position being oriented about 90° from said first position.

18. The apparatus according to claim 12, wherein said suture guide comprises a guide housing associated with said frame and having a suture guide aperture configured to guide a suture into the bore in the end face of the needle.

19. The apparatus according to claim 18, wherein said guide housing includes a suture release arm movably secured to said housing and in communication with said guide aperture such that movement of said release arm away from said guide aperture facilitates removal of the suture from said guide aperture subsequent to needle-suture attachment.

20. A method for attaching surgical suture components comprising:

positioning a surgical needle between at least one pair of dies of a needle impacting mechanism;

inserting a surgical suture into a bore in an end face of said surgical needle; and alternately moving said needle impacting mechanism in opposite directions between at least two positions relative to said surgical needle, wherein when said needle impacting mechanism is moved to said at least two positions, a drive member is actuated to cause said at least one pair of dies to impact said surgical needle and deform a portion of said surgical needle to maintain said surgical suture in said bore.

21. Apparatus for attaching a surgical suture to an eyeless needle comprising:

a support;

at least one pair of dies movably attached to the support for selectively impacting the needle such that a portion of the needle is deformed to maintain the suture therein, a first drive associated with said support;

a second drive associated with said support; and a suture guide adjacent the dies to guide the suture into a bore in the end face of the needle, the guide configured to facilitate removal of the attached needle suture from the apparatus; wherein the first drive moves the dies to impact the needle and the second drive reciprocally rotates the pair of dies between first and second positions relative to the needle.

* * * * *